United States Patent [19]

Hansen et al.

[11] Patent Number: 5,378,714
[45] Date of Patent: Jan. 3, 1995

[54] ANTIPSYCHOTIC PIPERIDINE DERIVATIVES

[75] Inventors: John B. Hansen, Jyderup; Lone Jeppesen, Virum; Frederik C. Gronvald, Vedb k, all of Denmark

[73] Assignee: Novo Nordisk A/S, Bagsvaerd, Denmark

[21] Appl. No.: 979,495

[22] Filed: Nov. 19, 1992

[30] Foreign Application Priority Data

Nov. 27, 1991 [WO] WIPO ............... PCT/DK91/00354

[51] Int. Cl.$^6$ ................ A61K 31/445; C07D 401/04; C07D 413/04; C07D 417/04
[52] U.S. Cl. .................. 514/321; 514/252; 514/322; 514/323; 544/368; 544/371; 546/197; 546/198; 546/199; 546/200; 546/201
[58] Field of Search ............ 546/198, 199, 197, 201, 546/200; 514/321, 322, 323, 255, 252; 544/368, 371

[56] References Cited

U.S. PATENT DOCUMENTS

| | | | |
|---|---|---|---|
| 3,576,810 | 4/1971 | Duncan et al. | 260/294 |
| 4,458,076 | 7/1984 | Strupczewski | 546/198 |
| 5,100,902 | 3/1992 | Peglion et al. | 514/321 |
| 5,143,923 | 9/1992 | Hrib | 546/199 |

FOREIGN PATENT DOCUMENTS

| | | |
|---|---|---|
| 0184258 | 6/1986 | European Pat. Off. . |
| 0368388 | 5/1990 | European Pat. Off. . |
| 0377528 | 7/1990 | European Pat. Off. . |
| 0402644 | 12/1990 | European Pat. Off. . |

OTHER PUBLICATIONS

Yevich et al., J. Med. Chem., vol. 29, pp. 359–369 (1986).

*Primary Examiner*—Celia Chang
*Attorney, Agent, or Firm*—Steve T. Zelson; Elias J. Lambiris

[57] ABSTRACT

The present invention relates to therapeutically active piperidine derivatives, of formula 1

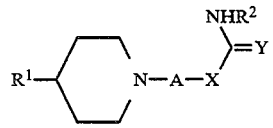

wherein, $R^1$, $R^2$, A, X and Y are as defined in the specification.

The compounds are useful in the treatment of indications related to the CNS-system, cardiovascular system or to gastrointestinal disorders.

17 Claims, No Drawings

ANTIPSYCHOTIC PIPERIDINE DERIVATIVES

Much evidence has accumulated to suggest that neuroleptics exert their antipsychotic action by blocking dopamine (DA) receptors in the brain. In recent years, it has become clear that some neuroleptics (e.g. clozapine) show an atypical profile: the compounds are not only beneficial in treating patients, who respond poorly to classical neuroleptic therapy, but the compounds are also relatively devoid of extrapyrimidal side effects (EPS) commonly seen with classical neuroleptics (Ereshefsky et al., Clin. Pharm 8, 691–709, 1989). In this respect it has been speculated that atypical neuroleptics are working mainly by blocking socalled A10 mesolimbic DA systems (areas which are thought to be affected in psychosis), while the side effects of classical neuroleptics are produced by blockade of DA receptors in the motor areas of the brain (A9 DA system (Gudelsky, Psychopharmacology (Berl) 99: S13–S17, 1989)). The antipsychotic effect of clozapine and related compounds might be due to its blockade of not only DA-receptors (D-1, D-2, D-3, D-4) but also 5HT-receptor subtypes ($5HT_2$-, $5HT_3$-, $5HT_{1C}$-, $5HT_{1A}$-), NA-$\alpha_1$- receptors, histamine and possibly other receptors.

Furthermore, $5HT_2$-blockade may also be important (Meltzer, Schizphr. Bull. 17: 263–87, 1991) to counteract the socalled negative symptoms of psychosis (delusions and social withdrawal) which are otherwise difficult to treat with conventional neuroleptics.

Compounds reducing 5-HT neurotransmission have been suggested to be useful for the treatment of various neurological and psychiatric diseases. $5HT_2$-antagonists, such as naftidrofuryl (Brain Res. 1989, 494(2) 387–90), are described to exhibit a protective effect on ischemic neuronal damage in the gerbil. Ritanserin, which is a potent and selective $5HT_2$-antagonist, has been shown to have anxiolytic-antidepressant activities in humans (Barone et al., Drug Clin. Pharm., 20 770 (1986)). Furthermore serotonergic mechanisms are described to be involved as active factors, or inducing processes, in the organization of sleep (Neuropharmacology, 19, 163 (1980)).

The piperidine derivative ketanserine, which is a $5HT_2$-antagonist with weak $\alpha_1$-blocking properties has been shown to be useful for treatment of various cardiovascular disorders.

Other similar piperidine derivatives are described in German Patent 1930818, EP 368388, EP 377528, EP 184258 and EP 402644.

This invention relates to piperidine derivatives, methods for making them and pharmaceutical compositions containing them.

The compounds of this invention demonstrate high affinity for various receptor subtypes including the $5HT_2$-, the NA-$\alpha_1$-, the dopamine $D_1$- and $D_2$-receptors or a combination of these. This invention relates to the use of said compounds as medicaments useful for treating CNS-system, cardiovascular system and gastrointestinal disorders, such as treatment of anxiety, sleep disorders, depression, psychosis, schizophrenia, migraine, ischemic neuronal damage, asthma, hypertension, urticaria, analgesia and emesis.

The present invention provides piperidine derivatives of formula I:

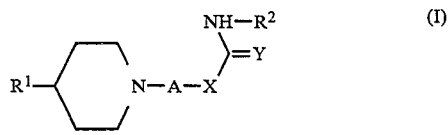

wherein A represents a straight or branched saturated hydrocarbon chain containing from 2 to 6 carbon atoms;
$R^1$ is

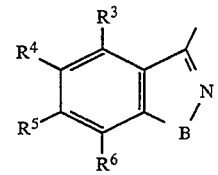

wherein $R^3$, $R^4$, $R^5$ and $R^6$ independently are hydrogen, halogen or $C_{1-6}$-alkyl;
B is —O— or —NH—; X is —O— or —NH—
is =O, =S or =NZ
wherein Z is hydrogen, $C_{1-6}$-alkyl or —CN;
$R^2$ is selected from the group consisting of

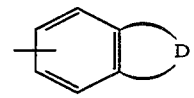

or

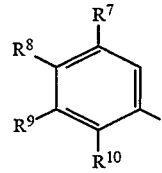

wherein $R^7$, $R^8$, $R^9$ and $R^{10}$ independently are hydrogen, $C_{1-6}$-alkyl, halogen,
- $C_{1-6}$-alkoxy or perhalomethyl;
—D— represents a 5- or 6-membered heterocycle containing one or more N-, O- or S-atoms, or a pharmaceutically acceptable salt thereof.

The purified reaction product may be converted into a physiologically acceptable salt. Such salts include acid addition salts formed with inorganic or organic acids, for example hydrochlorides, hydrobromides, sulphates, nitrates, oxalates, phosphates, tartrates, citrates, fumarates, maleates, succinates, and sulphonates e.g. mesylates. If desirable, selected salts may be subjected to further purification by recrystallization.

The invention includes within its scope all optical isomers of compounds of the general formula I and their mixtures including racemic mixtures thereof.

Specific compounds within the scope of the present invention include the following, or pharmaceutically acceptable salts thereof:

4-(6-Fluoro-1,2-benzisoxazol-3-yl)-1-[3-(6-indazolylcarbamoyloxy)propyl]piperidine, 4-(6-Fluoro-1,2-benzisoxazol-3-yl)-1-[3-(5-indazolylcarbamoyloxy)propyl]piperidine, 4-(6-Fluoro-1,2-benzisoxazol-3-yl)-1-[2-(5-indazolylcarbamoyloxy)ethyl]piperidine, 4-(6-Fluoro-1,2-benzisoxazol-3-yl)-1-[2-(6-indazolylcarbamoyloxy)ethyl]piperidine,
4-(6-Fluoro-1,2-benzisoxazol-3-yl)-1-[2-(6-(1-methylindazolyl)carbamoyloxy)ethyl]piperidine,
4-(6-Fluoro-1,2-benzisoxazol-3-yl)-1-[2-(5-(1-methylindazolyl)carbamoyloxy)ethyl]piperidine,
4-(6-Fluoro-1,2-benzisoxazol-3-yl)-1-[3-(6-indolylcarbamoyloxy)propyl]piperidine,
4-(6-Fluoro-1,2-benzisoxazol-3-yl)-1-[2-(6-indolylcarbamoyloxy)ethyl]piperidine,
4-(6-Fluoro-1,2-benzisoxazol-3-yl)-1-[3-(5-indolylcarbamoyloxy)propyl]piperidine,
4-(6-Fluoro-1,2-benzisoxazol-3-yl)-1-[2-(5-indolylcarbamoyloxy)ethyl]piperidine,
4-(6-Fluoro-1,2-benzisoxazol-3-yl)-1-[2-(5-(1-methylindolyl)carbamoyloxy)ethyl]piperidine,
4-(6-Fluoro-1,2-benzisoxazol-3-yl)-1-[3-(5-(1-methylindolyl)carbamoyloxy)propyl]piperidine,
4-(6-Fluoro-1,2-benzisoxazol-3-yl)-1-[3-(6-(1-methylindolyl)carbamoyloxy)propyl]piperidine,
4-(6-Fluoro-1,2-benzisoxazol-3-yl)-1-[2-(6-(1-methylindolyl)carbamoyloxy)ethyl]piperidine,
1-[3-(6-Benzoxazolylcarbamoyloxy)propyl]-4-(6-fluoro-1,2-benzisoxazol-3-yl)piperidine,
1-[2-(6-Benzoxazolylcarbamoyloxy)ethyl]-4-(6-fluoro-1,2-benzisoxazol-3-yl)piperidine,
1-[3-(5-Benzoxazolylcarbamoyloxy)propyl]-4-(6-fluoro-1,2-benzisoxazol-3-yl)piperidine,
1-[2-(5-Benzoxazolylcarbamoyloxy)ethyl]-4-(6-fluoro-1,2-benzisoxazol-3-yl)piperidine,
1-[2-(6-Benzothiazolylcarbamoyloxy)ethyl]-4-(6-fluoro-1,2-benzisoxazol-3-yl)piperidine,
1-[2-(6-Benzothiazolylthiocarbamoyloxy)ethyl]-4-(6-fluoro-1,2-benzisoxazol-3-yl)piperidine,
1-[3-(6-Benzothiazolylthiocarbamoyloxy)propyl]-4-(6-fluoro-1,2-benzisoxazol-3-yl)piperidine,
4-(6-Fluoro-1,2-benzisoxazol-3-yl)-1-[3-(6-(2-methylbenzothiazolyl)carbamoyloxy) propyl]piperidine,
4-(6-Fluoro-1,2-benzisoxazol-3-yl)-1-[2-(6-(2-methylbenzothiazolyl)carbamoyloxy) ethyl]piperidine,
1-[3-(5-Benzothiazolylcarbamoyloxy)propyl]-4-(6-fluoro-1,2-benzisoxazol-3-yl)piperidine,
1-[2-(5-Benzothiazolylcarbamoyloxy)ethyl]-4-(6-fluoro-1,2-benzisoxazol-3-yl)piperidine,
1-[3-(5-Benzothiazolylthiocarbamoyloxy)propyl]-4-(6-fluoro-1,2-benzisoxazol-3-yl)piperidine,
1-[2-(5-Benzothiazolylthiocarbamoyloxy)ethyl]-4-(6-fluoro-1,2-benzisoxazol-3-yl)piperidine,
4-(6-Fluoro-1,2-benzisoxazol-3-yl)-1-[2-(3,4,5-trimethoxyphenylcarbamoyloxy)ethyl]piperidine,
4-(6-Fluoro-1,2-benzisoxazol-3-yl)-1-[2-(3,4,5-trimethoxyphenylthiocarbamoyloxy) ethyl]piperidine,
4-(6-Fluoro-1,2-benzisoxazol-3-yl)-1-[3-(3,4,5-trimethoxyphenylthiocarbamoyloxy) propyl]piperidine,
1-[3-(3,4-Dimethoxyphenylcarbamoyloxy)propyl]-4-(6-fluoro-1,2-benzisoxazol-3-yl)piperidine,
1-[2-(3,4-Dimethoxyphenylcarbamoyloxy)ethyl]-4-(6-fluoro-1,2-benzisoxazol-3-yl)piperidine,
1-[2-(3,4-Dimethoxyphenylthiocarbamoyloxy)ethyl]-4-(6-fluoro-1,2-benzisoxazol-3-yl)piperidine,
1-[3-(3,4-Dimethoxyphenylthiocarbamoyloxy)propyl]-4-(6-fluoro-1,2-benzisoxazol-3-yl) piperidine,
1-[2-(3-Chloro-4-methoxyphenylcarbamoyloxy)ethyl]-4-(6-fluoro-1,2-benzisoxazol-3-yl) piperidine.
1-[2-(3-Chloro-4-methoxyphenylthiocarbamoyloxy)ethyl]-4-(6-fluoro-1,2-benzisoxazol-3-yl) piperidine,
1-[3-(3-Chloro-4-methoxyphenylthiocarbamoyloxy)propyl]-4-(6-fluoro-1, 2-benzisoxazol-3-yl)piperidine.

The invention also relates to methods of preparing the above mentioned compounds. These methods include reacting a compound of formula II

$$Y=C=N-R^2 \qquad (II)$$

wherein Y and $R^2$ have the meanings set forth above, with a compound of formula III

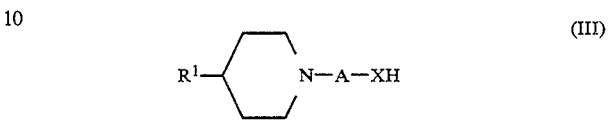

wherein A, X and $R^1$ have the meanings set forth above to form a compound of formula I.

For instance an isocyanate or isothiocyanate of 3,4,5-trimethoxybenzene, prepared by refluxing 3,4,5-trimethoxyaniline and phosgene or thiophosgene respectively in toluene, may be reacted with the desired piperidine alkylamine or piperidine alkylhydroxy intermediate to obtain the desired urea or carbamate of formula I.

Compounds of formula I, wherein X is —NH— and Y is =NZ wherein Z has the meanings set forth above are prepared by standard procedures as described in e.g. H. J. Petersen et al., J. Med. Chem. (1978) 21, 773–781, and R. Lee Webb et al., J. Heterocyclic Chem. 24, 275 (1987).

The procedure includes reacting a compound of formula IV

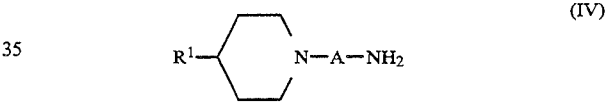

wherein A and $R^1$ have the meanings set forth above, with a compound of formula V

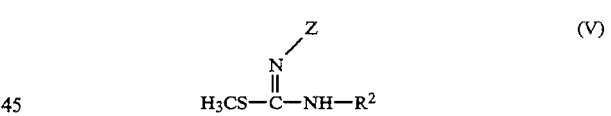

wherein $R^2$ and Z have the meanings set forth above, or reacting a compound of formula VI

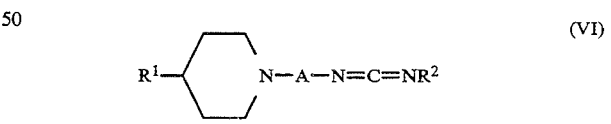

prepared by standard procedures, from a compound of formula VII

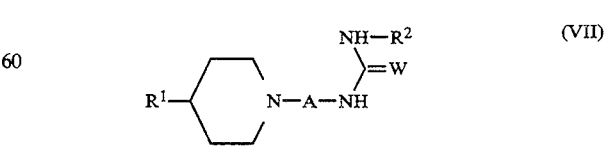

wherein A, $R^1$ and $R^2$ have the meanings set forth above and W is O or S, with $NH_2$—Z, wherein Z has the meaning set forth above, to form a compound of formula I, or reacting a compound of formula III, wherein X is —NH— and A and $R^1$ have the meanings set forth above, with a compound of formula VIII

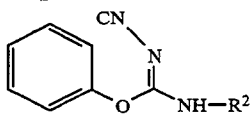 (VIII)

prepared by the method described in R. Lee Webb and C. S. Labaw, J. Heterocyclic Chem. 19, 1205 (1982) from $R^2$—$NH_2$ and N-cyanodiphenoxyimidocarbonate.

Compounds of formula III, wherein $R^1$, A and X have the meanings set forth above, have been prepared by alkylating the known piperidine IX (J. T. Strupc- zewski et al., J. Med. Chem., 28, 761–769 (1985))

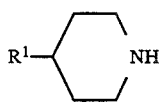 (IX)

wherein $R^1$ has the meaning set forth above, using standard procedures.

The compounds of the present invention were tested for binding to various CNS receptor subtypes as well as for analgesic activity in vitro in mice.

Detailed conditions for the in vitro and in vivo assays are described below:

IN-VITRO INHIBITION OF DOPAMINE D2 RECEPTOR BINDING

Method Description

Principle

Radioactive-labelled ligand $^3$H-Spiroperidol is incubated with isolated cell-membrane fragments at 37° C. for a given period of time. Following completed incubation, the incubate is filtered through GF/B filters which are rinsed following filtration to remove unspecifically adhered radioactivity. As opposed to low-molecular compounds, membrane fragments are not rinsed through the filters, the radioactivity bound to the filters is indicative of the amount of ligand bound specifically as well as nonspecifically to the membranes.

Tissue Preparation

The procedure is performed in ice bath. Polytron kinematica is rinsed with milli-Q-$H_2O$ before and after use. Male Wistar rats, 150–200 g are decapitated, striatum is removed quickly and weighed (approx. 50 mg). Striatum is transferred to a centrifuging vial containing 10 ml ice-cold D2 buffer. Homogenization is performed applying polytron kinematica (homogenizer) setting 6 for 20 sec. The homogenizer is rinsed with 10 ml D2 buffer in another centrifuging vial. The 10 ml rinsing buffer is added to the tissue vial. Centrifugation at 18,000 rpm for 10 min. at 4° C. Final pellet is transferred to 1,000×vol. of same buffer. (Ex. 50 mg striatum in 50 ml D2 buffer). Can be stored at 0° C. for at least 4 hours. Note that the tissue must be monogeneous (uniform) before use. If not, brief homogenization is performed.

Assay 2,500 µl tissue (homogeneous)

25 µl $^3$H-Spiroperidol (0.05 nM)

25 µl test substance/$H_2O$/blind (Domperidone 0.2 µM)

Incubation for 20 min. at 37° C.—10 min. on ice bath.

10 ml ice-cold 0.9% NaCl is added to the tubes and filtered through GF/B filters (use gloves). This procedure is repeated. The filters are placed in counting vials and 4 ml opti-flour is added (perform in fume cupboard, use gloves). Counting is performed at window 0–19 of the beta-counter (Pachard). Note that receptor box and lid are rinsed thoroughly in $H_2O$ after use to avoid contamination. Further, the analytical site is cleaned carefully every day after use.

Test Substances

Dissolved in $H_2O$, EtOH, MeOH or DMSO and further diluted in $H_2O$. The D2 binding will stand concentrations of up to approx. 20% of these solvents without affecting the binding. Most stock solutions are stable at 4° C., attention is, however, paid to any precipitation, change in colour etc. Test-substance dilutions are always made fresh every day. When weighing out test substances, it is attempted to weigh out approx. 1 mg of substance. Less than 0.8 mg must never be weighed out and only infrequently more than 2 mg (for economy reasons), dependent, however, on conc./assay.

Results

The test value is given as $IC_{50}$ indicating the concentration inhibiting specific binding by 50%.

IN-VITRO INHIBITION OF $α_1$-RECEPTOR BINDING

Method Description

Principle

Radioactive-labelled ligand $^3$H-Prazosin is incubated with isolated cell-membrane fragments at 25° C. for a given period of time. Following completed incubation, the incubate is filtered through GF/B filters, which are rinsed following filtration to remove unspecifically adhered radioactivity. As opposed to low-molecular compounds, membrane fragments are not rinsed through the filters, the radioactivity bound to the filters indicates the amount of ligand bound specifically as well as nonspecifically to the membranes.

Tissue Preparation

The procedure is performed in ice bath. Polytron kinematica is rinsed with milli-Q-$H_2O$ before and after use. Male Wistar rats, 150–200 g are decapitated, cortex is removed quickly and weighed (approx. 500 mg). Cortex is transferred to a centrifuging vial containing 10 ml ice-cold D2 buffer. Homogenization applying polytron kinematica (homogenizer) setting 6 for 20 sec. The homogenizer is rinsed with 10 ml D2 buffer in another centrifuging vial. The 10 ml rinsing buffer is added to the tissue vial. Centrifugation at 18,000 rpm for 12 min. at 4° C. This is repeated once. Final pellet is added to 400×vol. of same buffer. (ex. 500 mg cortex in 200 ml D2 buffer). Can be stored for 30 min. at 0° C.

Assay 2,000 µl tissue

25 µl $^3$H-Prazosin (0.5 nM)

25 µl test substance/$H_2O$/blind Phentolamine (10/µM)

Incubation for 30 min. at 25° C.

10 ml of ice-cold 0.9% NaCl is added to the tubes and filtered through GF/B filters (use gloves). This procedure is repeated. Filters are placed in counting vials and 4 ml opti-flour is added (perform in fume cupboard, use gloves). Counting is performed at window 0–19 of the beta-counter (Pachard). Note that receptor box and cover are rinsed thoroughly in $H_2O$ after use to avoid contamination. Further, the analytical site is cleaned carefully every day after use.

Test Substances

Dissolved in H₂O, EtOH, MeOH or DMSO and further diluted in H₂O. The binding will stand concentrations of up to approx. 5% of these solvents without affecting the binding. Most stock solutions are stable at 4° C. Attention is, however, paid to any precipitation, change in colour etc. Test-substance dilutions are always made fresh every day. When weighing out test substances, it is attempted to weigh out approx. 1 mg of substance. Less than 0.8 mg must never be weighed out and only infrequently more than 2 mg (for economy reasons), dependent, however, on conc./assay.

Results

The test value is given as $IC_{50}$ indicating the concentration inhibiting specific binding by 50%.

IN-VITRO INHIBITION OF DOPAMINE D1RECEPTOR BINDING

Method Description

Principle

Radioactive-labelled ligand $^3$H-SCH 23390 is incubated with isolated cell-membrane fragments in incubation buffer at 30° C. for a given period of time. Following completed incubation, the incubate is filtered through GF/B filters, which are rinsed following filtration to remove unspecifically adhered radioactivity. As opposed to low-molecular compounds, membrane fragments are not rinsed through the filters, the radioactivity bound to the filters indicates the amount of ligand bound specifically as well as nonspecifically to the membranes.

Tissue Preparation

Male Wistar rats, 150–200 g are decapitated. Striatum is removed quickly, weighed (approx. 50 mg) arid carefully homogenized in 100×vol. of buffer I applying glass/teflon homogenizer 10 up/down strokes. Ex.: 50 mg striatum is homogenized in 5,000 μl buffer I. The homogenate is centrifuged at 8,000 rpm for 20 min. at 4° C., and the supernate is decanted. This step is performed three times, and each time the pellet is resuspended and homogenized in 100×vol. of buffer I. Following the third centrifugation, the pellet is suspended in 100×vol. of resuspension buffer and homogenized. The tissue is now ready for use. The tissue is stable at 0° C. for 8 hours.

Assay

600 μl incubation buffer
100 μl $^3$H-SCH 23390 (0.2 nM)
100 μl tissue
200 μl test substance/H₂O/blind (cis-flupentixol 2 μM)

Incubation for 60 min. at 30° C.

10 ml of ice-cold 0.9% NaCl is added to the tubes. Filtration is performed through GF/B filters (use gloves). This procedure is repeated. Filters are placed in counting vials and 4 ml opti-flour is added (perform in fume cupboard, use gloves) and counting is performed at window 0–19 of the beta-counter (Pachard). Note that receptor box and lid are rinsed thoroughly in H₂O after use to avoid contamination. Further, the analytical site is cleaned carefully every day after use.

Test Substances

Dissolved in H₂O, EtOH, MeOH or DMSO and further diluted in H₂O. The D1binding will stand concentrations of up to approx. 20% of these solvents without affecting the binding. Most stock solutions are stable at 4° C. Attention should, however, be paid to any precipitation, change in colour etc. Test-substance dilutions are always made fresh every day. When weighing out test substances, it is attempted to weigh out approx. 1 mg of substance. Less than 0.8 mg must never be weighed out and only infrequently more than 2 mg (for economy reasons), dependent, however, on conc./assay.

Results

The test value is given as $IC_{50}$ indicating the concentration inhibiting specific binding by 50%.

IN VITRO INHIBITION OF 5HT₂RECEPTOR BINDING

Method Description

Principle

Radioactive-labelled ligand $^3$H-Ketanserine is incubated with isolated cell membrane fragments at 37° C. for a given period of time. Following completed incubation, the incubate is filtered through GF/B filters, which are rinsed following filtration to remove unspecifically adhered radioactivity. As opposed to low-molecular compounds, membrane fragments are not rinsed through the filters, the radioactivity bound to the filters indicates the amount of ligand bound specifically as well as nonspecifically to the membranes.

Tissue Preparation

The preparation is made in ice bath. Polytron kinematica is rinsed with milli-Q-H₂O before and after use. Male Wistar rats, 150–200 g are decapitated.

Frontal cortex is removed quickly and weighed (approx. 200 mg). Frontal cortex is added to centrifuging vial containing 10 ml ice-cold D2 buffer. Homogenization applying polytron kinematica (homogenizer) setting 6 for 20 sec. The homogenizer is rinsed with 10 ml D2 buffer in another centrifuging vial. The 10 ml rinsing buffer is added to the tissue vial. Centrifuged at 18,000 rpm for 10 min. at 4° C. Final pellet is transferred to 125×vol. of same buffer. (Ex 200 mg in 25 ml D2 buffer). Can be stored for approx. 30 min. at 0° C.

Assay

1250 μl tissue
25 μl $^3$H-Ketanserine (0.4 nM)
25 μl test substance/H₂O/blind cyproheptadine (2 μM)

Incubation for 15 min. at 37° C.

10 ml ice-cold 0.9% NaCl is added to the tubes. Filtration is performed through GF/B filters (use gloves). This procedure is repeated. The filters are placed in counting vials and 4 ml opti-flour is added (prepare in fume cupboard, use gloves). Counting at window 0–19 of the beta-counter (Pachard). Note that receptor box and lid are rinsed thoroughly in H₂O after use to avoid contamination. Further, the analytical site is cleaned carefully every day.

Test Substances

Dissolved in H₂O, EtOH, MeOH or DMSO and further diluted in H₂O. The 5HT₂ binding will stand concentrations of up to approx. 5% of these solvents without affecting the binding. Most stock solutions are stable at 4° C. Attention should, however, be paid to any precipitation, change in colour etc. Test-substance dilutions are always made fresh every day. When weighing out test substances, it is attempted to weigh out approx. 1 mg of substance. Less than 0.8 mg must never be weighed out and only infrequently more than 2 mg (for economy reasons), dependent, however, on conc./assay.

Results

The test value is given as $IC_{50}$ i.e. the concentration inhibiting specific binding by 50%.

ANTAGONISM OF ACETIC ACID-INDUCED -WRITHINGS IN MICE

Principle

In mice i.p. injection of acetic acid induces a writhing syndrome which is antagonized by analgesics (Siegmund et al., 1957; Eckhardt et al., 1957).

Method:

Acetic acid 0.5 per cent is injected i.p. (0.15 ml/10 g body weight) to 6 mice (NMRI, either sex weighing 20–25 g) pretreated with physiological saline (controls) and to 6 mice pretreated with test substance. In the controls acetic acid induces a syndrome characterized by contraction of abdomen, turning of trunk and extension of hind limbs. Saline and test substances are administered s.c. 30 min. before acetic acid. The number of writhings is counted 5–15 min. after injection of acetic acid.

Results

Initially, the dose of test substance is equivalent to 5–10 per cent of $LD_{50}$. If this dose decreases writhings, 3–5 dose levels are tested. The activity is expressed as per cent protection:

$$100 - \frac{\text{average writhings of treated group}}{\text{average writhings of daily control groups}} \times 100$$

The effect of active substances is evaluated by a dose response curve, log dose on the abscissa, and per cent protection on the ordinate. The potency is expressed as the dose ($ED_{50}$ in mg/kg) giving 50 per cent protection against writhings.

Specificity of Test

Analgesics and various other drugs inhibit acetic acid-induced writhings in mice. This test is used as a screening test for analgesics. Additional results from other screening tests are required to exclude active anti-writhing substances without analgesic effect.

References

Eckhardt, E. et al. Ethiology of chemically induced writhing in mouse and rat. Proc. Soc. exp. Biol. 98, 186–188, 1958.

Siegmund, E. et al. A method for evaluating both non-narcotic and narcotic analgesics. Proc. Soc. exp. Biol. 95, 729–731, 1957.

The compounds of this invention typically binds to NA-$\alpha_1$, $5HT_2$-, DA-$D_1$-, and DA-$D_2$-receptors, with $IC_{50}$ values in the order of 0.1 nM to 1 $\mu$M. Furthermore the compounds are able to antagonize the acetic acid induced writhing in mice with $ED_{50}$-values typically in the order of 0.1 mg/kg to 100 mg/kg.

The compounds of the invention, together with a conventional adjuvant, carrier, or diluent, and if desired a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compound of the invention is dispensed in unit dosage form comprising 0.05–100 mg in a pharmaceutically acceptable carrier per unit dosage.

A typical tablet which may be prepared by conventional tabletting techniques contains:

| | |
|---|---|
| Active compound | 1.0 mg |
| Lactosum | 67.8 mg Ph. Eur. |
| Avicel ® | 31.4 mg |
| Amberlite ® IRP 88 | 1.0 mg |
| Magnesii stearas | 0.25 mg Ph. Eur. |

The following examples illustrate the specific methods employed in production of a representative number of compounds embraced by this invention.

EXAMPLE 1

4-(6-Fluoro-1,2-benzisoxazol-3-yl)-1-[3-(3,4,5-trimethoxyphenylcarbamoyloxy)propyl]piperidine, Oxalate A. 4-(6-Fluoro-1,2-benzisoxazol-3-yl)piperidine, hydrochloride (5.0 g, 20 mmol), 3-bromopropanol (2.0 ml, 21.6 mmol) and potassium carbonate (6.5 g, 47 mmol) in 300 ml dry acetone were refluxed for 16 h. The mixture was cooled to room temperature, filtered and concentrated in vacuo. The resulting compound was recrystallized from ethanol/water to give 4.3 g of the desired compound. M.p. 139°–141° C.

B. A mixture of 3,4,5-trimethoxyaniline (365 mg; 2.0 mmol) in toluene (20 ml) and phosgene (6 ml 20% in toluene; 12 mmol) was refluxed for 6 h. The solvent was removed under reduced pressure to give crude 3,4,5-trimethoxyphenylisocyanate. To the crude product was added 3(4-(6-fluoro-1,2-benzisoxazol-3-yl)-piperidine) propanol (420 mg; 1.5 mmol) in DMF (10 ml). The mixture was stirred at 100° C. for 2 h and then at room temperature for 16 h, whereupon it was taken up in ethyl acetate and water. The organic phase was washed with water and saturated sodium chloride and concentrated in vacuo. The resulting oil was taken up in acetone/ethanol (4:1, v/v) and oxalic acid (150 mg) in 2 ml acetone added to precipitate the desired product. The product was washed with ice cold ethanol giving 550 mg of the title compound. M.p. 77°–80° C. MS (70 eV): m/z 487 (9%, M+), 287 (31), 233 (40), 209 (56), 194 (45), 140 (67), 96 (100).

EXAMPLE 2

4-(6-Fluoro-1,2-benzisoxazol-3-yl)-1-[3-(3,4-ethylenedioxyphenylcarbamoyloxy) propyl]piperidine, Oxalate A mixture of 1,4-benzodioxan-6-amine (300 mg; 2.0 mmol) in toluene (20 ml) and phosgene (10 ml 20% in toluene; 19 mmol) was refluxed for 6 h. The solvent was removed under reduced pressure to give crude 3,4-ethylenedioxyphenylisocyanate. To the crude product was added 3-[4-(6-fluoro-1,2-benzisoxazol-3-yl) piperidino]propanol (420 mg; 1.5 mmol) in DMF (10 ml). The mixture was stirred at 100° C. for 2 h and then at room temperature for 16 h, whereupon it was taken up in ethyl acetate and water. The organic phase was washed with water and saturated sodium chloride and concentrated in vacuo. The resulting oil was taken up in acetone/ethanol (4:1, v/v) and oxalic acid (150 mg) in 2 ml acetone added to precipitate the desired product. The product was washed with ice cold ethanol to give 600 mg of the title compound. M.p. 109°–110° C. MS (70 eV): m/z 455 (32%, M+), 278 (23), 233 (49), 177 (89), 140 (48), 121 (42), 96 (100).

EXAMPLE 3

1-[3-(6-Benzothiazolylcarbamoyloxy)propyl]-4-(6-fluoro-1,2-benzisoxazol-3-yl)piperidine, Oxalate A mixture of 6-aminobenzothiazole (300 mg; 2 mmol) in toluene (20 ml) and phosgene (10 ml 20% in toluene, 19 mmol) was refluxed for 6 h. The solvent was removed under reduced pressure to give crude 6-benzothiazolylisocyanate. Using the procedure of example 1 the crude 6-benzothiazolylisocyanate was combined with 3-[4-(6-fluoro-1,2-benzisoxazol-3-yl)-piperidino]-propanol (410 mg; 1.5 mmol) in 10 ml DMF to give the 0.7 g of the title compound. M.p. 176°–177° C. MS (70 eV): m/z 454 (3%, M+), 27 (25), 233 (30), 190 (17), 176 (55), 150 (37), 140 (53), 96 (100).

EXAMPLE 4

1-[3-(3,4-Ethylenedioxyphenylthiocarbamoyloxy)-propyl]-4-(6-fluoro-1,2-benzisoxazol-3-yl) piperidine, Oxalate To a mixture of 1,4-benzodioxan-6-amine (15.1 g; 100 mmol) and triethylamine (20.2 g; 200 mmol) in toluene (350 ml) was added dropwise over 10 min. thiophosgene (11.5 g; 100 mmol) in toluene (50 ml). The mixture was stirred at 80° C. for 30 min., cooled to room temperature and filtered. The filtrate was evaporated. The product was redissolved in toluene and concentrated in vacuo. The resulting oil was taken up in warm petroleum ether, which was filtered. The filtrate was concentrated to a small volume, which afforded 7.2 g of 3,4-ethylenedioxyphenylisothiocyanate.

Starting from 3,4-ethylenedioxyphenylisothiocyanate (390 mg; 2.0 mmol) and 3-[4-(6-fluoro-1,2-benzisoxazol-3-yl)piperidino]propanol (420 mg; 1.5 mmol) using the procedure described in example 1 was prepared 550 mg of the title compound: M.p. 101°–104° C. MS (70 eV): m/z 471 (0.5%, M+), 278 (61), 233 (58), 193 (100), 151 (17), 140 (60).

EXAMPLE 5

4-(6-Fluoro-1,2-benzisoxazol-3-yl)-1-[2-(3,4,5-trimethoxyphenylcarbamoyloxy)ethyl]piperidine, Oxalate A. 4-(6-Fluoro-1,2-benzisoxazol-3-yl)piperidine, hydrochloride (2.6 g, 10 mmol), 2-bromoethanol (1.3 ml, 15 mmol) and potassium carbonate (4.1 g, 30 mmol) in 25 ml dry acetone were refluxed for two hours and then stirred at 60° C. for 16 h, whereupon extra 0.4 ml (5 mmol) 2-bromoethanol was added. The mixture was then refluxed for 4 h, cooled to room temperature, concentrated in vacuo and taken up in water and methylene chloride. The organic phase was washed with water and saturated sodium chloride, dried over MgSO$_4$ and concentrated in vacuo. Purification by column chromatography (silica gel; methylene chloride:methanol:conc. ammonium hydroxide (80:20:0.5, v/v/v)) gave 2.2 g of 2-[4(6-fluoro-1,2-benzisoxazol-3-yl)piperidino]ethanol. M.p. 119°–120° C.

B. Starting from 3,4,5-trimethoxyphenylisocyanate (600 mg, 3 mmol) and 2-[4-(6-fluoro-1,2-benzisoxazol-3-yl)-piperidino]ethanol (400 mg; 1.5 mmol) using the procedure described in example 1 was prepared 450 mg of the title compound. M.p. 158°–160° C. MS (70 eV): m/z 473 (32%, M+), 246 (38), 233 (100), 209 (41).

EXAMPLE 6

1-(3-(6-Benzthiazolylthiocarbamoyloxy)propyl)-4-(6-fluoro-1,2-benzisoxazol-3-yl)piperidine, Oxalate Using the procedure described in example 4 starting from 3-[4-(6-fluoro-1,2-benzisoxazol-3-yl) piperidino]-propanol (280 mg, 1.0 mmol) and 6-benzothiazolylisothiocyanate (210 mg, 1.2 mmol), prepared from 6-aminobenzothiazole and thiophosgene, was prepared 280 mg of the title compound. M.p. 108°–112° C., MS (70 eV): m/z 470 (0.2%, M+), 278, (38), 233 (30), 192 (62) 150 (65), 140 (75), 96 (100).

EXAMPLE 7

4-(6-Fluoro-1,2-benzisoxazol-3-yl)-1-(3-(3,4-methylenedioxyphenylcarbamoyloxy)propyl) piperidine, Oxalate Using the procedure described in example 1 starting from 3-[4-(6-fluoro-1,2-benzisoxazol-3-yl) piperidino]-propanol (140 mg, 0.5 mmol) and 3,4-methylenedioxyphenylisocyanate (240 mg, 1.5 mmol), prepared from 3,4-methylenedioxyaniline and phosgene, was prepared 210 mg of the title compound. M.p. 133°–136° C. MS (70 eV): m/z 441 (20%, M+), 303 (15), 278 (16), 233 (53), 163 (52), 140 (37), 96 (100).

EXAMPLE 8

1-[2-(6-Benzothiazolylcarbamoyloxy)ethyl]-4-(6-fluoro-1,2-benzisoxazol-3-yl)piperidine, Oxalate Using the procedure of example 3 crude 6-benzothiazolylisocyanate, prepared from 6-aminobenzothiazole (500 mg, 3.4 mmol), was combined with 2-[4-(6-fluoro-1,2-benzisoxazol-3-yl)piperidino]ethanol (450 mg, 1.7 mmol) in 10 ml dry DMF to give 100 mg of the title compound. M.p. 130°–134° C. MS (70 eV): m/z 440 (1%, M+), 264 (23), 233 (69), 150 (100).

EXAMPLE 9

4-(6-Fluoro-1,2-benzisoxazol-3-yl)-1-[2-(3,4-methylenedioxyphenylcarbamoyloxy)ethyl]piperidine, Hydrochloride Starting from 3,4-methylenedioxyphenylisocyanate (320 mg, 2 mmol) and 2-[4-(6-fluoro-1,2-benzisoxazol-3-yl)piperidino]ethanol (270 mg, 1 mmol) in 5 ml dry DMF using the procedure described in example 1 was prepared 210 mg of the title compound as free base. This product was dissolved in 5 ml ethanol/acetone (50%, v/v) and ethanolic hydrochloric acid added to precipitate 180 mg of the desired product as white crystals. M.p. 226°–229° C. MS (70 eV): m/z 428 (47%, M+), 246 (42), 233 (100), 208 (21), 190 (47), 163 (70).

EXAMPLE 10

4-(6-Fluoro-1,2-benzisoxazol-3-yl)-1-[3-(phenylcarbamoyloxy)propyl]piperidine, Hydrochloride Phenylisocyanate (0.36 g, 3 mmol) and 3-[4-(6-fluoro-1,2-benzisoxazol-3-yl)piperidino]propanol (0.3 g, 1.1 mmol) was refluxed in toluene (25 ml) for 6 h. The mixture was cooled to room temperature and hydrochloric acid in ether was added. The resulting precipitate was recrystallized from ethanol/ether and isopropanol/ether to give 180 mg of the title compound as white crystals. M.p. 204.5°–205.5° C. MS (70 eV): m/z 397 (39%, M+), 278 (4), 259 (26), 233 (50), 178 (28), 96 (100).

EXAMPLE 11

N-Cyano-N'-(3,4-methylenedioxyphenyl)-N''-3-(4-((6-fluoro-1,2-benzisoxazol-3-yl)piperidino)propyl) guanidine, Oxalate A mixture of N-cyanodiphenoxyimidocarbonate (1.2 g, 5 mmol), 3,4-methylenedioxyaniline (0.7 g, 5 mmol) and 2-propanol (25 ml) was stirred at room temperature for 16 h. The formed precipitate was taken up in methylene chloride, treated with activated carbon. Evaporation of the solute and trituration with ether gave 1.2 g of N-cyano-N'-3,4-methylenedioxyphenyl-O-phenylisourea. M.p. 172°–174° C.

1-(3-Aminopropyl)-4-(6-fluoro-1,2-benzisoxazol-3-yl)piperidine (420 mg, 1.1 mmol), N-cyano-N'-3,4-methylenedioxyphenyl-O-phenylisourea (320 mg, 1.2 mmol), 0.4 ml triethyl amine and 25 ml 2-propanol were stirred at room temperature for 4 days. The mixture was concentrated in vacuo and then taken up in water and methylene chloride. The organic phase was washed with water and saturated sodium chloride, dried over magnesium sulphate and concentrated in vacuo. The product was purified by column chromatography (silica gel; ethyl acetate:methanol (4:1, v/v)), and then taken up in 2 ml dry acetone. Oxalic acid (50 mg) in 1 ml acetone was added precipitating 90 mg of the desired product as white crystals. M.p. 112°–115° C. MS (70 eV): m/z 464 (M+, 1%), 422 (4), 233 (10), 220 (32), 137 (100).

EXAMPLE 12

1-[3-(3,4-Methylenedioxyphenylcarbamoyloxy)propyl]-4-(6-fluoro-1H-indazol-3-yl) piperidine A. To a mixture of 6-fluoro-3-(4-piperidinyl)-1H-indazole (438 mg, 2 mmol) and dry potassium carbonate (1.1 g, 6 mmol) in 30 ml methyl isobutyl ketone was added 3-bromo-1-propanol (276 mg, 2 mmol). The mixture was refluxed for 48 h, cooled, filtered and concentrated in vacuo. The crude product was purified by chromatography on silica gel 60 eluting with ethyl acetate:methanol (9:1, v/v). Concentration of the appropriate fractions afforded 300 mg (53%) of 3-[1-(1-hydroxyprop-3-yl)-4-piperidinyl]-6-fluoro-1 H-indazole as an oil.

$^1$H-NMR (DMSO-d$_6$, δ): 1.62 (t, 2H), 1.7–2.1 (br., 8H), 2.39 (t, 2H), 2.95 (br., 3H), 3.48 (t, 2H), 6.90 (dt, 1H), 7.21 (dd, 1H), 7.78 (q, 1H), 12.70 (s, 1H).

B. A solution of 3-[1-(1-hydroxyprop-3-yl)-4-piperidinyl]-6-fluoro-1H-indazole (230 mg, 0.83 mmol) in 5 ml dry DMF was added 3,4-methylenedioxyphenylisocyanate (291 mg, 1.65 mmol) in 3 ml dry DMF. The reaction was heated to 100° C. for 2 h and 16 h at 80° C. The reaction was cooled to room temperature and added a mixture of 50 ml water and 200 ml ether, filtered and separated. The ether phase was washed with water, brine and dried with sodium sulphate and concentrated in vacuo. The crude product was purified by chromatography on silica gel 60 eluting with ethyl acetate:methanol (9:1, v/v). Concentration of the appropriate fractions afforded 50 mg (11%) of the title compound as an amorphous solid.

$^1$H-NMR (DMSO-d$_6$, δ): 1.71–1.92 (m, 6H), 2.1 (m, 2H), 2.42 (br., 2H), 2.98 (br.d, 3H), 4.11 (t, 2H), 5.95 (s, 2H), 6.82 (m, 2H), 6.91 (t, 1H), 7.14 (s, 1H), 7.21 (dd, 1H), 7.80 (dt, 1H), 9.5 (s, 1H), 12.68 (s, 1H).

Analysis: $C_{23}H_{25}N_4O_4F$, 0.75 $H_2O$: Calculated: C 60.85; H 5.88; N 12.34%. Found: C 60.69; H 5.76; N 12.31%.

MS (70 eV): m/z 440 (M+, 1%), 277 (14), 232 (100), 218 (12), 189 (37), 163 (80), 70 (16).

EXAMPLE 13

1-[2-(3,4-Methylenedioxyphenylcarbamoyloxy)propyl]-4-(6-fluoro-1H-indazol-3-yl) piperidine A. A mixture of 6-fluoro-3-(4-piperidinyl)-1H-indazole (500 mg, 2.3 mmol) and propylene oxide (1g, 17 mmol) in 25 ml toluene was heated to 50° C. in an autoclave for 7 days. The cooled reaction was concentrated in vacuo and purified by chromatography on silica gel 60 eluting with ethyl acetate:methanol (4:1, v/v). Concentration of the appropriate fractions afforded 350 mg (54.9%) of 3-[1-(2-hydroxyprop-1-yl)-4-piperidinyl]-6-fluoro-1 H-indazole as a foam.

$^1$H-NMR (DMSO-d$_6$, δ): 1.04 (d, 3H), 1.87 (m, 4H), 2.18 (m, 4H), 2.93 (br. d, 3H), 3.78 (m, 1H), 4.25 (br., 1H), 6.91 (dt, 1H), 7.20 (dd, 1H), 7.78 (q, 1 H), 12.58 (s, 1H).

B. Starting from 3-[1-(2-hydroxyprop-1-yl)-4-piperidinyl]-6-fluoro-1H-indazole (300 mg, 1.1 mmol) and 3,4-methylenedioxyphenylisocyanate (380 mg, 2.2 mmol) using the procedure described in example 12A was prepared 40 mg (9%) of the title compound as an amorphous solid.

1H-NMR (DMSO-d6, δ): 1.21 (d, 3H), 1.85 (m, 4H), 2.20 (m, 2H), 2.4 (m, 1H), 2.55 (m, 1H), 3.0 (m, 2H), 3.1 (m, 1H), 4.9 (m, 1H), 5.98 (s, 2H), 6.8 (d, 1H), 6.89 (m,2H), 7.14 (s, 1H), 7.19 (dd, 1H), 7.73 (dt, 1H), 9.51 (s, 1H), 12.68 (s, 1H).

MS (70 eV): m/z 441 (M++, 1.1%), 440 (M+, 1), 259 (29), 232 (100), 218 (7), 189 (48), 163 (41), 137 (15).

EXAMPLE 14

1-[6-(3,4-Methylenedioxyphenylcarbamoyloxy)hexyl]-4-(6-fluoro-1,2-benzisoxazol-3-yl) piperidine A. A mixture of 6-fluoro-3-(4-piperidinyl)-1,2-benzisoxazole hydrochloride (1g, 3.9 mmol), lithium carbonate (865 mg, 1.7 mmol) and 6-chloro-1-hexanol (534 mg, 3.9 mmol) in 5 ml dry DMF was heated at 100° C. for 48 h. The reaction was poured into water and the aqueous mixture was extracted with ethyl acetate. The ethyl acetate phase was washed with water, brine, dried with sodium sulphate and concentrated in vacuo. The crude product was purified by chromatography on silica gel 60 eluting with ethyl acetate:methanol (9:1, v/v). Concentration of the appropriate fractions afforded 310 mg (25.6%) of 3-[1-(1-hydroxyhex-6-yl)-4-piperidinyl]-6-fluoro-1, 2-benzisoxazole as an oil.

1H-NMR (CDCl3, δ): 1.39 (m, 4H), 1.58 (m, 4H), 2.10 (m, 6H), 2.41 (t, 2H), 3.09 (br.d, 3H), 3.65 (t, 2H), 7.04 (dt, 1H), 7.23 (dd, 1H), 7.75 (q, 1H).

MS (70 eV): m/z 320 (M+, 28%), 233 (47), 190 (15), 182 (50), 96 (100), 82 (100), 82 (21), 55 (23).

B. Starting from 3-[1-(1-hydroxyhex-6-yl]-4-piperidinyl]-6-fluoro-1,2-benzisoxazole (270 mg, 0.84 mmol) and 3,4-methylenedioxyphenylisocyanate (297 mg, 1.69 mmol) using the procedure described in example 12B was prepared 210 mg (51.8%) of the title compound as an amorphous solid.

1H-NMR (CDCl3, δ): 1.4 (m, 4H), 1.6 (m, 4H), 2.11 (m, 6H), 2.42 (t, 2H), 3.09 (br.d, 3H), 4.15 (t, 2H), 5.95 (s, 2H), 6.70 (m, 2H), 7.05 (m, 2H), 7.24 (m, 2H), 7.72 (q, 1H).

MS (70 eV): m/z 483 (M+, 1.5%), 320 (22), 233 (45), 182 (32), 163 (100), 130 (75), 96 (70), 77 (35).

EXAMPLE 15

4-(6-Fluoro-1,2-benzisoxazol-3-yl)-1-(3-(2-bromo-4,5-methylenedioxyphenylcarbamoyloxy) propyl)piperidine, Hydrochloride 4-(6-Fluoro-1,2-benzisoxazol-3-yl)-1-(3-(3,4-methylenedioxyphenylcarbamoyloxy)propyl)piperidine (example 7) (220 mg, 0.5 mmol) was dissolved in 2 ml glacial acetic acid and the mixture stirred at room temperature under $N_2$. $Br_2$ (0.25 μl, 0.5 mmol) dissolved in 1.0 ml glacial acetic acid was added. The mixture was stirred for 2 h whereupon aqueous $K_2CO_3$ was added to neutralize the solution, which was then extracted with ethyl acetate. The organic phase was dried over magnesium sulphate and concentrated in vacuo. The product was taken up in acetone and HCl in ether added to crystallize the desired product as 40 mg white crystals. M.p. 215°-218° C. MS (70 eV): m/z 521 (17%, M+), 519 (17%, M+), 278 (20), 243 (35), 241 (34), 233 (56), 96 (100).

EXAMPLE 16

4-(6-Fluoro-1,2-benzisoxazol-3-yl)-1-(3-(3,4-methylenedioxyphenylthiocarbamoyloxy)propyl) piperidine, Hydrochloride 3,4-Methylenedioxyphenylisothiocyanate (360 mg, 2 mmol) and 3-[4-(6-fluoro-1, 2-benzisoxazol-3-yl)piperidino]propanol (4.20 mg, 1.5 mmol) in 5 ml dry DMF were stirred at 100° C. for 2 h and then at 60° C. for 16 h. The mixture was cooled to room temperature and taken up between water and ether. The organic phase was washed with water and saturated sodium chloride, dried over magnesium sulphate and concentrated in vacuo. Purification of the product by column chromatography (silicagel; ethyl acetate:methanol (4:1, v/v)) gave an oil, which was taken up in dry acetone. HCl in ether was added to crystallize the desired product as 550 mg white crystals. M.p. 181°-185° C. MS (70 eV): m/z 457 (1%, M+), 278 (55), 233 (56), 179 (100).

EXAMPLE 17

4-(6-Fluoro-1,2-benzisoxazol-3-yl)-1-(3-(2-methoxyphenyl)carbamoyloxy)propyl)piperidine, Hydrochloride 2-Methoxyphenylisocyanate (270 mg, 2 mmol) and 3-[4-(6-fluoro-1,2-benzisoxazol-3-yl) piperidino]propanol (280 mg, 1 mmol) was dissolved in 100 ml dry toluene and refluxed for 16 h. 50 ml ethyl acetate was added to the cooled mixture, which was then washed with water and saturated sodium chloride. 2.5 ml (1.9 M) HCl in ethanol was added and the solution was concentrated to about 30 ml crystallizing 310 mg of the desired product. M.p. 174°-175° C. MS (70 eV): m/z 427 (30%, M+), 289 (19), 233 (33), 96 (100).

EXAMPLE 18

4-(6-Fluoro-1,2-benzisoxazol-3-yl)-1-(3-(3-chloro-4-methoxyphenyl)carbamoyloxy)propyl) piperidine, Hydrochloride Starting from 3-chloro-4-methoxyphenylisocyanate, prepared from 3-chloro-4-methoxyaniline (470 mg, 3 mmol) and phosgene (7.5 mmol) as described in example 1, and 3-[4-(6-fluoro-1,2-benzisoxazol-3-yl)piperidino]propanol (560 mg, 2 mmol) using the procedure of example 1, was prepared 500 mg mg of the desired product. M.p. 212°-215° C.

EXAMPLE 19

1-[2-(3,4-Methylenedioxyphenylcarbamoyloxy) propyl]-4-(6-fluoro-1,2-benzisoxazol-3-yl) piperidine, Oxalate A. A mixture of 6-fluoro-3-(4-piperidinyl)-1,2-benzisoxazol (1.5 g, 6.8 mmol) and propylene oxide; (2 g, 34.4 mmol) in 25 ml acetonitrile was heated to 50° C. in an autoclave for 3 days. The cooled reaction was concentrated in vacuo and purified by chromatography on silica gel 60 eluting with ethyl acetate:methanol (9:1, v/v). Concentration of the appropriate fraction afforded 1.3 g (68.4%) of 3-[1-(2-hydroxyprop-1-yl)-4-piperidinyl]-6-fluoro-1, 2-benzisoxazole. M.p. 45°-47° C. MS (70 eV): m/z 278 (M+, 18%), 233 (100), 190 (28), 109 (12), 96 (70), 82 (25), 68 (14), 55 (22).

B. Starting from 3-[1-(2-hydroxyprop-1-yl)-4-piperidinyl]-6-fluoro-1,2-benzisoxazole (500 mg, 1.1 mmol) and 3,4-methylenedioxyphenylisocyanate (500 mg, 2.2 mmol) using the procedure described in example 12B was prepared 100 mg (17%) of the title compound. M.p. 163°-164° C. MS (70 eV): m/z 441 (M+, 11%), 260 (32), 233 (100), 190 (25), 163 (17), 136 (33), 96 (58).

Analysis: $C_{25}H_{26}N_3FO_9$, 0.5 $H_2O$. Calculated: C 55.55; H 5.03; N 7.77%. Found: C 55.74; H 4.91; N 7.39%

We claim:

1. A compound of formula I

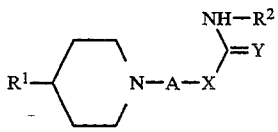

wherein

A is a straight or branched saturated hydrocarbon chain containing from 2 to 6 carbon atoms;

$R^1$ is

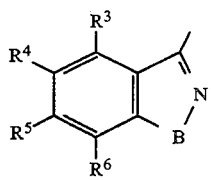

wherein $R^3$, $R^4$, $R^5$ and $R^6$ independently are hydrogen, halogen or $C_{1-6}$-alkyl;

B is —O— or —NH—;

X is —O— or —NH—;

Y is O, S or NZ wherein Z is hydrogen, $C_{1-6}$-alkyl or —CN;

$R^2$ is selected from the group consisting of

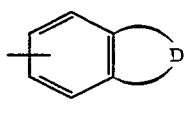

or

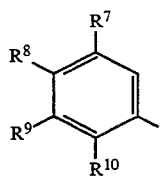

wherein $R^7$, $R^8$, $R^9$ and $R^{10}$ independently are hydrogen, $C_{1-6}$-alkyl, halogen, $C_{1-6}$-alkoxy or perhalomethyl; and —D— is a pyrrolo, pyrazolo, thiazolo oxazolo, isoxazolo, 1,3-dioxolo or 1,4-dioxano group; or a pharmaceutically acceptable salt thereof.

2. The compound according to claim 1, wherein B is O.

3. The compound according to claim 1, wherein $R^3$, $R^4$ and $R^6$ are hydrogen and $R^5$ is fluorine.

4. The compound according to claim 1, wherein X is O and Y is O, S or NCN.

5. The compound according to claim 1, wherein $R^2$ is

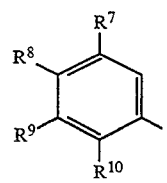

wherein $R^7$, $R^8$, $R^9$ and $R^{10}$ independently are hydrogen or methoxy.

6. The compound according to claim 2, wherein $R^3$, $R^4$ and $R^6$ are hydrogen and $R^5$ is fluorine.

7. The compound according to claim 2, wherein X is O and Y is O, S or NCN.

8. The compound according to claim 2, wherein $R^2$ is

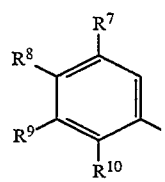

wherein $R^7$, $R^8$, $R^9$ and $R^{10}$ independently are hydrogen or methoxy.

9. A compound according to claim 1 which is
4-(6-Fluoro-1,2-benzisoxazol-3-yl)-1-[3-(3,4,5-trimethoxyphenylcarbamoyloxy)propyl]piperidine;
4-(6-Fluoro-1,2-benzisoxazol-3-yl)-1-[2-(3,4,5-trimethoxyphenylcarbamoyloxy)ethyl]piperidine;
4-(6-Fluoro-1,2-benzisoxazol-3-yl)-1-[3-(phenylcarbamoyloxy)propyl]piperidine;
4-(6-Fluoro-1,2-benzisoxazol-3-yl)-1-(3-(2-methoxyphenylcarbamoyloxy)propyl) piperidine;
4-(6-Fluoro-1,2-benzisoxazol-3-yl)-1-(3-(3-chloro-4-methoxyphenylcarbamoyloxy)propyl) piperidine;
or a pharmaceutically acceptable salt thereof.

10. A compound according to claim 1 which is
4-(6-Fluoro-1,2-benzisoxazol-3-yl)-1-[3-(3,4-ethylenedioxyphenylcarbamoyloxy)propyl]piperidine;
1-[3-(3,4-Ethylenedioxyphenylthiocarbamoyloxy)-propyl]-4-(6-fluoro-1,2-benzisoxazol-3-yl) piperidine;
4-(6-Fluoro-1,2-benzisoxazol-3-yl)-1-(3-(3,4-methylenedioxyphenylcarbamoyloxy)propyl)-piperidine;
4-(6-Fluoro-1,2-benzisoxazol-3-yl)-1-[2-(3,4-methylenedioxyphenylcarbamoyloxy]ethyl]piperidine;
N-Cyano-N'-(3,4-methylenedioxyphenyl)-N''-3-((6-fluoro-1,2-benzisoxazol-3-yl)piperidino)propyl) guanidine;
1-[6-(3,4-Methylenedioxyphenylcarbamoyloxy)hexyl]-4-(6-fluoro-1,2-benzisoxazol-3-yl) piperidine;
4-(6-Fluoro-1,2-benzisoxazol-3-yl)-1-(3-(3,4-methylenedioxyphenylthiocarbamoyloxy)propyl) piperidine;
1-[2-(3,4-Methylenedioxyphenylcarbamoyloxy)-propyl]-4-(6-fluoro-1,2-benzisoxazol-3-yl) piperidine;
or a pharmaceutically acceptable salt thereof.

11. A compound according to claim 1 which is
1-[3-(6-Benzothiazolylcarbamoyloxy)propyl]-4-(6-fluoro-1,2-benzisoxazol-3-yl)piperidine;

1-(3-(6-Benzothiazolylthiocarbamoyloxy)propyl)-4-(6-fluoro-1,2-benzisoxazol-3-yl)piperidine;

1-[2-(6-Benzothiazolylcarbamoyloxy)ethyl]-4-(6-fluoro-1,2-benzisoxazol-3-yl)piperidine;

or a pharmaceutically acceptable salt thereof.

12. A compound according to claim 1 which is

1-[3-(3,4-Methylenedioxyphenylcarbamoyloxy)-propyl]-4-(6-fluoro-1H-indazol-3-yl)piperidine;

1-[2-(3,4-Methylenedioxyphenylcarbamoyloxy)-propyl]-4-(6-fluoro-1H-indazol-3-yl)piperidine;

or a pharmaceutically acceptable salt thereof.

13. A compound which is 4-(6-(Fluoro-1,2-benzisoxazol-3-yl)-1-(3-(2-bromo-4, 5-methylenedioxy or a pharmaceutically acceptable salt thereof.

14. A pharmaceutical composition, comprising an antipsychotic effective amount of a compound according to claim 1 together with a pharmaceutically acceptable carrier or diluent.

15. The pharmaceutical composition which is in the form of an oral dosage unit containing about 0.05–100 mg of the compound according to claim 1.

16. A method of treating psychosis, comprising administering to a subject in need thereof an effective amount of a compound according to claim 1.

17. A method of treating psychosis, comprising administering to a subject in need thereof a pharmaceutical composition according to claim 14.

* * * * *